US008840646B2

(12) United States Patent
Vittur et al.

(10) Patent No.: US 8,840,646 B2
(45) Date of Patent: Sep. 23, 2014

(54) SPINOUS PROCESS IMPLANTS AND METHODS

(75) Inventors: Shannon Marlece Vittur, Memphis, TN (US); Aurelien Bruneau, Memphis, TN (US); Eric C. Lange, Collierville, TN (US); Kent M. Anderson, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1507 days.

(21) Appl. No.: 11/801,587

(22) Filed: May 10, 2007

(65) Prior Publication Data

US 2008/0281360 A1 Nov. 13, 2008

(51) Int. Cl.
*A61B 17/70* (2006.01)
*A61F 2/44* (2006.01)
*A61F 2/30* (2006.01)

(52) U.S. Cl.
CPC ......... *A61F 2/44* (2013.01); *A61F 2002/30772* (2013.01); *A61B 17/7062* (2013.01)
USPC ...................................................... 606/247

(58) Field of Classification Search
USPC .......... 606/246–253, 280–299; 403/391, 396, 403/399
See application file for complete search history.

(56) References Cited

U.S. PATENT DOCUMENTS

| | | |
|---|---|---|
| 2,677,369 A | 5/1954 | Knowles |
| 3,397,699 A | 8/1968 | Kohl |
| 3,648,691 A | 3/1972 | Lumb et al. |
| 4,011,602 A | 3/1977 | Rybicki et al. |
| 4,257,409 A | 3/1981 | Bacal et al. |
| 4,327,736 A | 5/1982 | Inoue |
| 4,554,914 A | 11/1985 | Kapp et al. |
| 4,573,454 A | 3/1986 | Hoffman |
| 4,604,995 A | 8/1986 | Stephens et al. |
| 4,686,970 A | 8/1987 | Dove et al. |
| 4,721,103 A | 1/1988 | Freedland |
| 4,827,918 A | 5/1989 | Olerud |
| 5,011,484 A | 4/1991 | Breard |
| 5,047,055 A | 9/1991 | Bao et al. |
| 5,092,866 A | 3/1992 | Breard et al. |
| 5,201,734 A | 4/1993 | Cozad et al. |
| 5,306,275 A | 4/1994 | Bryan |
| 5,316,422 A | 5/1994 | Coffman |

(Continued)

FOREIGN PATENT DOCUMENTS

| | | |
|---|---|---|
| DE | 2821678 A1 | 11/1979 |
| EP | 0322334 B1 | 2/1992 |

(Continued)

OTHER PUBLICATIONS

"Dispositivo Intervertebrale Ammortizzante DIAM," date unknown, p. 1.
"Tecnica Operatoria Per II Posizionamento Della Protesi DIAM," date unknown, pp. 1-3.
"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.
Aota et al., "Postfusion Instability at the Adjacent Segments After Rigid Pedicle Screw Fixation for Degenerative Lumbar Spinal Disorders," J. Spinal Dis., Dec. 1995, pp. 464-473, vol. 8, No. 6.

(Continued)

*Primary Examiner* — Jan Christopher Merene
*Assistant Examiner* — Steven Cotroneo (57) ABSTRACT

Devices and methods for replacing one or more spinous processes of a patient include a replacement body with a lamina portion positionable anteriorly toward the spinal canal along with a spinous process portion extending posteriorly from the lamina portion to replace a removed spinous process. Connecting elements extend from opposite sides of the body for connection to the vertebral body with anchors.

28 Claims, 4 Drawing Sheets

(56) References Cited

U.S. PATENT DOCUMENTS

| | | | |
|---|---|---|---|
| 5,360,430 A | 11/1994 | Lin | |
| 5,366,455 A | 11/1994 | Dove | |
| 5,415,661 A | 5/1995 | Holmes | |
| 5,437,672 A | 8/1995 | Alleyne | |
| 5,454,812 A | 10/1995 | Lin | |
| 5,496,318 A | 3/1996 | Howland et al. | |
| 5,609,634 A | 3/1997 | Voydeville | |
| 5,628,756 A | 5/1997 | Barker, Jr. et al. | |
| 5,645,599 A | 7/1997 | Samani | |
| 5,674,295 A | 10/1997 | Ray et al. | |
| 5,676,702 A | 10/1997 | Ratron | |
| 5,690,649 A | 11/1997 | Li | |
| 5,702,452 A | 12/1997 | Argenson et al. | |
| 5,810,815 A | 9/1998 | Morales | |
| 5,836,948 A | 11/1998 | Zucherman et al. | |
| 5,860,977 A | 1/1999 | Zucherman et al. | |
| 5,976,186 A | 11/1999 | Bao et al. | |
| 6,022,376 A | 2/2000 | Assell et al. | |
| 6,048,342 A | 4/2000 | Zucherman et al. | |
| 6,068,630 A | 5/2000 | Zucherman et al. | |
| 6,074,390 A | 6/2000 | Zucherman et al. | |
| 6,132,464 A | 10/2000 | Martin | |
| 6,214,037 B1 | 4/2001 | Mitchell et al. | |
| 6,293,949 B1 | 9/2001 | Justis et al. | |
| 6,352,537 B1 | 3/2002 | Strnad | |
| 6,364,883 B1 | 4/2002 | Santilli | |
| 6,402,750 B1 | 6/2002 | Atkinson et al. | |
| 6,419,703 B1 * | 7/2002 | Fallin et al. | 623/17.11 |
| 6,440,169 B1 | 8/2002 | Elberg et al. | |
| 6,451,019 B1 | 9/2002 | Zucherman et al. | |
| 6,500,178 B2 | 12/2002 | Zucherman et al. | |
| 6,514,256 B2 | 2/2003 | Zucherman et al. | |
| 6,582,433 B2 | 6/2003 | Yun | |
| 6,626,944 B1 | 9/2003 | Taylor | |
| 6,645,207 B2 | 11/2003 | Dixon et al. | |
| 6,669,729 B2 * | 12/2003 | Chin | 623/17.11 |
| 6,695,842 B2 | 2/2004 | Zucherman et al. | |
| 6,699,246 B2 | 3/2004 | Zucherman et al. | |
| 6,709,435 B2 | 3/2004 | Lin | |
| 6,723,126 B1 | 4/2004 | Berry | |
| 6,733,534 B2 | 5/2004 | Sherman | |
| 6,761,720 B1 | 7/2004 | Senegas | |
| 6,811,567 B2 | 11/2004 | Reiley | |
| 6,835,205 B2 | 12/2004 | Atkinson et al. | |
| 6,902,580 B2 * | 6/2005 | Fallin et al. | 623/17.11 |
| 6,946,000 B2 | 9/2005 | Senegas et al. | |
| 6,974,478 B2 * | 12/2005 | Reiley et al. | 623/17.11 |
| 7,041,136 B2 | 5/2006 | Goble et al. | |
| 7,048,736 B2 | 5/2006 | Robinson et al. | |
| 7,087,083 B2 | 8/2006 | Pasquet et al. | |
| 7,090,698 B2 | 8/2006 | Goble et al. | |
| 7,097,654 B1 | 8/2006 | Freedland | |
| 7,101,375 B2 | 9/2006 | Zucherman et al. | |
| 7,163,558 B2 | 1/2007 | Senegas et al. | |
| 7,201,751 B2 | 4/2007 | Zucherman et al. | |
| 7,238,204 B2 | 7/2007 | Le Couedic et al. | |
| 7,306,628 B2 | 12/2007 | Zucherman et al. | |
| 7,335,203 B2 | 2/2008 | Winslow et al. | |
| 7,377,942 B2 | 5/2008 | Berry | |
| 7,442,208 B2 | 10/2008 | Mathieu et al. | |
| 7,445,637 B2 | 11/2008 | Taylor | |
| 7,563,274 B2 * | 7/2009 | Justis et al. | 606/279 |
| 7,604,652 B2 | 10/2009 | Arnin et al. | |
| 7,658,752 B2 * | 2/2010 | Labrom et al. | 606/249 |
| 7,749,252 B2 | 7/2010 | Zucherman et al. | |
| 7,771,456 B2 | 8/2010 | Hartmann et al. | |
| 7,862,615 B2 | 1/2011 | Carli et al. | |
| 7,901,430 B2 | 3/2011 | Matsuura et al. | |
| 2001/0016743 A1 | 8/2001 | Zucherman et al. | |
| 2002/0143331 A1 | 10/2002 | Zucherman et al. | |
| 2003/0045940 A1 | 3/2003 | Eberlein et al. | |
| 2003/0065330 A1 | 4/2003 | Zucherman et al. | |
| 2003/0153915 A1 | 8/2003 | Nekozuka et al. | |
| 2004/0097931 A1 | 5/2004 | Mitchell | |
| 2004/0106995 A1 | 6/2004 | Le Couedic et al. | |
| 2004/0117017 A1 | 6/2004 | Pasquet et al. | |
| 2004/0133280 A1 | 7/2004 | Trieu | |
| 2004/0199255 A1 | 10/2004 | Mathieu et al. | |
| 2005/0010293 A1 | 1/2005 | Zucherman et al. | |
| 2005/0033434 A1 * | 2/2005 | Berry | 623/17.14 |
| 2005/0049708 A1 | 3/2005 | Atkinson et al. | |
| 2005/0070932 A1 | 3/2005 | Falahee | |
| 2005/0165398 A1 | 7/2005 | Reiley | |
| 2005/0203512 A1 | 9/2005 | Hawkins et al. | |
| 2005/0203624 A1 | 9/2005 | Serhan et al. | |
| 2005/0228391 A1 | 10/2005 | Levy et al. | |
| 2005/0234551 A1 | 10/2005 | Fallin et al. | |
| 2005/0245929 A1 | 11/2005 | Winslow et al. | |
| 2005/0261768 A1 | 11/2005 | Trieu | |
| 2005/0267579 A1 * | 12/2005 | Reiley et al. | 623/17.11 |
| 2005/0288672 A1 | 12/2005 | Ferree | |
| 2006/0004447 A1 | 1/2006 | Mastrorio et al. | |
| 2006/0015181 A1 | 1/2006 | Elberg | |
| 2006/0036324 A1 | 2/2006 | Sachs et al. | |
| 2006/0058790 A1 | 3/2006 | Carl et al. | |
| 2006/0064165 A1 | 3/2006 | Zucherman et al. | |
| 2006/0079896 A1 | 4/2006 | Kwak et al. | |
| 2006/0084983 A1 | 4/2006 | Kim | |
| 2006/0084985 A1 | 4/2006 | Kim | |
| 2006/0084987 A1 | 4/2006 | Kim | |
| 2006/0084988 A1 | 4/2006 | Kim | |
| 2006/0084991 A1 | 4/2006 | Borgstrom et al. | |
| 2006/0085069 A1 | 4/2006 | Kim | |
| 2006/0085070 A1 | 4/2006 | Kim | |
| 2006/0085074 A1 | 4/2006 | Raiszadeh | |
| 2006/0089654 A1 | 4/2006 | Lins et al. | |
| 2006/0089719 A1 | 4/2006 | Trieu | |
| 2006/0106381 A1 | 5/2006 | Ferree et al. | |
| 2006/0106397 A1 | 5/2006 | Lins | |
| 2006/0111728 A1 | 5/2006 | Abdou | |
| 2006/0122620 A1 | 6/2006 | Kim | |
| 2006/0129239 A1 | 6/2006 | Kwak | |
| 2006/0136060 A1 | 6/2006 | Taylor | |
| 2006/0142759 A1 | 6/2006 | Arnin et al. | |
| 2006/0149229 A1 | 7/2006 | Kwak et al. | |
| 2006/0149242 A1 | 7/2006 | Kraus et al. | |
| 2006/0161154 A1 | 7/2006 | McAfee | |
| 2006/0182515 A1 | 8/2006 | Panasik et al. | |
| 2006/0184247 A1 | 8/2006 | Edidin et al. | |
| 2006/0184248 A1 | 8/2006 | Edidin et al. | |
| 2006/0195102 A1 | 8/2006 | Malandain | |
| 2006/0217718 A1 | 9/2006 | Chervitz et al. | |
| 2006/0217726 A1 | 9/2006 | Maxy et al. | |
| 2006/0224159 A1 | 10/2006 | Anderson | |
| 2006/0235387 A1 | 10/2006 | Peterman | |
| 2006/0235532 A1 | 10/2006 | Meunier et al. | |
| 2006/0241601 A1 | 10/2006 | Trautwein et al. | |
| 2006/0241610 A1 | 10/2006 | Lim et al. | |
| 2006/0241613 A1 | 10/2006 | Bruneau et al. | |
| 2006/0241757 A1 | 10/2006 | Anderson | |
| 2006/0247623 A1 | 11/2006 | Anderson et al. | |
| 2006/0247640 A1 | 11/2006 | Blackwell et al. | |
| 2006/0264938 A1 | 11/2006 | Zucherman et al. | |
| 2006/0271044 A1 | 11/2006 | Petrini et al. | |
| 2006/0271049 A1 | 11/2006 | Zucherman et al. | |
| 2006/0282075 A1 * | 12/2006 | Labrom et al. | 606/61 |
| 2006/0282079 A1 * | 12/2006 | Labrom et al. | 606/61 |
| 2006/0293662 A1 | 12/2006 | Boyer, II et al. | |
| 2006/0293663 A1 | 12/2006 | Walkenhorst et al. | |
| 2007/0005064 A1 | 1/2007 | Anderson et al. | |
| 2007/0010813 A1 | 1/2007 | Zucherman et al. | |
| 2007/0043362 A1 | 2/2007 | Malandain et al. | |
| 2007/0043363 A1 | 2/2007 | Malandain et al. | |
| 2007/0100340 A1 | 5/2007 | Lange et al. | |
| 2007/0123861 A1 | 5/2007 | Dewey et al. | |
| 2007/0162000 A1 | 7/2007 | Perkins | |
| 2007/0167945 A1 | 7/2007 | Lange et al. | |
| 2007/0173822 A1 | 7/2007 | Bruneau et al. | |
| 2007/0173823 A1 | 7/2007 | Dewey et al. | |
| 2007/0191833 A1 | 8/2007 | Bruneau et al. | |
| 2007/0191834 A1 * | 8/2007 | Bruneau et al. | 606/61 |
| 2007/0191837 A1 | 8/2007 | Trieu | |
| 2007/0198091 A1 | 8/2007 | Boyer et al. | |
| 2007/0233068 A1 | 10/2007 | Bruneau et al. | |

(56) References Cited

U.S. PATENT DOCUMENTS

| | | | |
|---|---|---|---|
| 2007/0233074 A1 | 10/2007 | Anderson et al. | |
| 2007/0233076 A1 | 10/2007 | Trieu | |
| 2007/0233081 A1 | 10/2007 | Pasquet et al. | |
| 2007/0233089 A1 | 10/2007 | DiPoto et al. | |
| 2007/0250060 A1 | 10/2007 | Anderson et al. | |
| 2007/0270823 A1 | 11/2007 | Trieu et al. | |
| 2007/0270824 A1 | 11/2007 | Lim et al. | |
| 2007/0270825 A1 | 11/2007 | Carls et al. | |
| 2007/0270826 A1 | 11/2007 | Trieu et al. | |
| 2007/0270827 A1 | 11/2007 | Lim et al. | |
| 2007/0270828 A1 | 11/2007 | Bruneau et al. | |
| 2007/0270829 A1 | 11/2007 | Carls et al. | |
| 2007/0270834 A1 | 11/2007 | Bruneau et al. | |
| 2007/0270874 A1 | 11/2007 | Anderson | |
| 2007/0272259 A1 | 11/2007 | Allard et al. | |
| 2007/0276368 A1 | 11/2007 | Trieu et al. | |
| 2007/0276496 A1 | 11/2007 | Lange et al. | |
| 2007/0276497 A1 | 11/2007 | Anderson | |
| 2008/0021460 A1 | 1/2008 | Bruneau et al. | |
| 2008/0097446 A1* | 4/2008 | Reiley et al. | 606/69 |
| 2008/0114357 A1 | 5/2008 | Allard et al. | |
| 2008/0114358 A1 | 5/2008 | Anderson et al. | |
| 2008/0114456 A1 | 5/2008 | Dewey et al. | |
| 2008/0147190 A1 | 6/2008 | Dewey et al. | |
| 2008/0161818 A1 | 7/2008 | Kloss et al. | |
| 2008/0167685 A1 | 7/2008 | Allard et al. | |
| 2008/0195152 A1 | 8/2008 | Altarac et al. | |
| 2008/0215094 A1 | 9/2008 | Taylor | |
| 2008/0281360 A1 | 11/2008 | Vittur et al. | |
| 2008/0281361 A1 | 11/2008 | Vittur et al. | |
| 2009/0062915 A1 | 3/2009 | Kohm et al. | |
| 2009/0105773 A1 | 4/2009 | Lange et al. | |
| 2009/0204151 A1 | 8/2009 | Bracken | |
| 2009/0216276 A1 | 8/2009 | Pasquet | |
| 2009/0240283 A1 | 9/2009 | Carls et al. | |
| 2010/0121379 A1 | 5/2010 | Edmond | |
| 2010/0204732 A1 | 8/2010 | Aschmann et al. | |
| 2010/0211101 A1 | 8/2010 | Blackwell et al. | |

FOREIGN PATENT DOCUMENTS

| | | |
|---|---|---|
| EP | 1138268 A1 | 10/2001 |
| EP | 1330987 A1 | 7/2003 |
| EP | 1854433 A1 | 11/2007 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2 799 948 | 10/1999 |
| FR | 2816197 A1 | 5/2002 |
| FR | 2799948 A1 | 4/2007 |
| JP | 02-224660 | 9/1990 |
| JP | 09-075381 | 3/1997 |
| JP | 2003-079649 | 3/2003 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 98/20939 | 5/1998 |
| WO | WO 2004/047691 A1 | 6/2004 |
| WO | WO 2004/084743 A1 | 10/2004 |
| WO | WO 2005/009300 A1 | 2/2005 |
| WO | WO 2005/044118 A1 | 5/2005 |
| WO | WO 2005/110258 A1 | 11/2005 |
| WO | WO 2006/064356 A1 | 6/2006 |
| WO | WO 2007/034516 A1 | 3/2007 |

OTHER PUBLICATIONS

Benzel et al., "Posterior Cervical Interspinous Compression Wiring and Fusion for Mid to Low Cervical Spinal Injuries," J. Neurosurg., Jun. 1989, pp. 893-899, vol. 70.

Booth et al., "Complications and Predictive Factors for the Successful Treatment of Flatback Deformity (Fixed Sagittal Imbalance)," SPINE, 1999, pp. 1712-1720, vol. 24, No. 16.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertebral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maitrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysairè Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

(56) References Cited

OTHER PUBLICATIONS

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Societa di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rahm et al., "Adjacent-Segment Degeneration After Lumbar Fusion with Instrumentation: A Retrospective Study," J. Spinal Dis., Oct. 1996, pp. 392-400, vol. 9, No. 5.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schären et al, "Erfolge and Probleme langstreckiger Fusionen der degenerativen Lendenwirbelsäule," Osteosynthese International, Jul. 17, 1998, pp. 173-179, vol. 6, Johann Ambrosius Barth.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "Lumbar Motion Segment Pathology Adjacent to Thoracolumbar, Lumbar, and Lumbosacral Fusions," SPINE, Apr. 15, 1996, pp. 970-981, vol. 21, No. 8.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medecine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link América Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Anasetti et al., "Spine Stability After Implantation of an Interspinous Device: An In Vitro and Finite Element Biomechanical Study," J. Neurosurg. Spine, Nov. 2010, vol. 13, pp. 568-575.

Bellini et al., "Biomechanics of the Lumbar Spine After Dynamic Stabilization," J. Spinal Disord. Tech., 2006, vol. 00, No. 00, pp. 1-7.

Buric et al., "DIAM device for Low Back Pain in Degenerative Disc Disease 24 Months Follow-up," Acta Neurochirurgica Supplementum, 2011, vol. 108, pp. 177-182.

Kramer et al., "Intervetertebral Disk Diseases: Causes, Diagnosis, Treatment and Prophylaxis," pp. 244-249, Medical, 1990.

Phillips et al., "Biomechanics of Posterior Dynamic Stabilizing Device (DIAM) After Facetectorny and Discectomy," The Spine Journal, 2006, vol. 6, pp. 714-722.

Taylor et al., "Device for Intervertebral Assisted Motion: Technique and Initial Results," Neurosurg. Focus, Jan. 2007, vol. 22, pp. 1-6.

Wilke et al., "Biomechanical Effect of Different Lumbar Interspinous Implants on Flexibility and Intradiscal Pressure," Eur. Spine J., vol. 17, published online Jun. 27, 2008, pp. 1049-1056.

Zdeblick et al., "Two-Point Fixation of the Lumbar Spine Differential Stability in Rotation," SPINE, 1991, pp. S298-S301, vol. 16, No. 6, Supplement.

Zhao et al., "Efficacy of the Dynamic Interspinous Assisted Motion System in Clinical Treatment of Degenerative Lumbar Disease," Chin. Med. J., 2010, 123(21), pp. 2974-2977.

* cited by examiner

SPINOUS PROCESS IMPLANTS AND METHODS

BACKGROUND

Spinal stabilization procedures are performed and include placement of devices between vertebral bodies in the disc space or along the spinal column. For example, varieties of inter-body fusion devices are widely used following partial or total discectomies to fuse adjacent vertebrae. Artificial disc devices can be placed in the disc space if motion preservation is desired. Still other stabilization devices contemplate the attachment of plates, rods or tethers extradiscally along the vertebrae. Still others are positioned between spinous processes.

In some procedures, the spinous process of the patient may be damaged or otherwise compromised such that it is not capable of supporting an interspinous stabilization element in a stabilization procedure. There remains a need for devices for spinal stabilization that replace the spinous process so that interspinous stabilization procedures can be completed even if the spinous process of the patient is compromised.

SUMMARY

Devices and methods for replacing one or more spinous processes of a patient include a replacement body with a lamina portion positionable anteriorly toward the spinal canal along with a spinous process portion extending posteriorly from the lamina portion to replace a removed spinous process. Connecting elements extend from opposite sides of the body for connection to the vertebral body with anchors.

According to one aspect, an artificial spinous process implant includes a replacement body with a lamina portion and a spinous process portion. The lamina portion lies generally along an anterior side of the replacement body and extends from a superior end of the replacement body to an inferior end of the replacement body. The lamina portion also includes opposite lateral sides extending between the superior and inferior ends of the replacement body. The spinous process portion is located between the lateral sides of the lamina portion and extends from said lamina portion toward a posterior side of the replacement body opposite the anterior side. The spinous process portion further extends between the superior and inferior ends of the replacement body while in a transverse orientation to the first plane.

According to another aspect, an artificial spinous process implant includes a replacement body. The replacement body includes a lamina portion lying along an anterior side of the replacement body that extends in a direction from a superior end of the replacement body toward an inferior end of the replacement body. The lamina portion further includes opposite lateral sides extending in a direction between the superior end and the inferior end of the replacement body. The replacement body also includes a spinous process portion extending from the lamina portion toward a posterior side of the replacement body opposite the anterior side. The spinous process portion further extends in a direction between the superior and inferior ends of the replacement body. The implant also includes a pair of elongated connecting elements extending in opposite directions from the replacement body and away from the spinous process portion.

According to a further aspect, a method for stabilizing adjacent vertebrae of a spinal column comprises: accessing the spinal column from a posterior approach; removing at least a portion of at least one spinous process and/or lamina of a vertebra; engaging an artificial spinous process implant to the vertebra; and positioning an interspinous implant between the artificial spinous process implant and a spinous process of a second vertebra adjacent to the vertebra.

In another aspect, an artificial spinous process implant includes at least one through-hole for receiving a tether to secure an interspinous implant thereto.

In another aspect, an artificial spinous process implant includes at least one notch for engagement by a distractor instrument to apply distraction forces between the vertebra to which the implant is engaged and an adjacent vertebra.

In another aspect, an artificial spinous process implant includes lateral support members extending along opposite sides of a spinous process portion of the implant to provide support for an interspinous implant engaged to the artificial spinous process implant. In one form, interspinous implants are engaged to the spinous process portion on superior and inferior sides of the pair of lateral support members.

In another aspect, an artificial spinous process implant includes a replacement body with a lamina portion and a spinous process portion. The spinous process portion includes opposite sides tapering in width from a mid-portion of the spinous process portion toward at least one of the superior and inferior ends of the replacement body.

In another aspect, a posterior spinal stabilization system includes a replacement body engageable to a first vertebra and an interspinous spacer implant engageable to the spinous replacement body and a spinous process of a second vertebra.

These and other aspects will be discussed further below.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Spinous process implants include a replacement body implantable adjacent to the spinal column to replace a spinous process of a vertebra. The replacement body can also reinforce or replace all or a portion of a lamina resected, removed, or altered along with the spinous process. The replacement body of the implant includes a lamina portion positionable adjacent the spinal canal and in contact with or adjacent to the lamina. The replacement body also includes a spinous process portion extending posteriorly from the lamina portion to replace the removed spinous process. The replacement body includes connecting elements extending therefrom for engagement with anchors or other devices engaged to the vertebral body to secure the replacement body in position in the patient.

Figure 1:
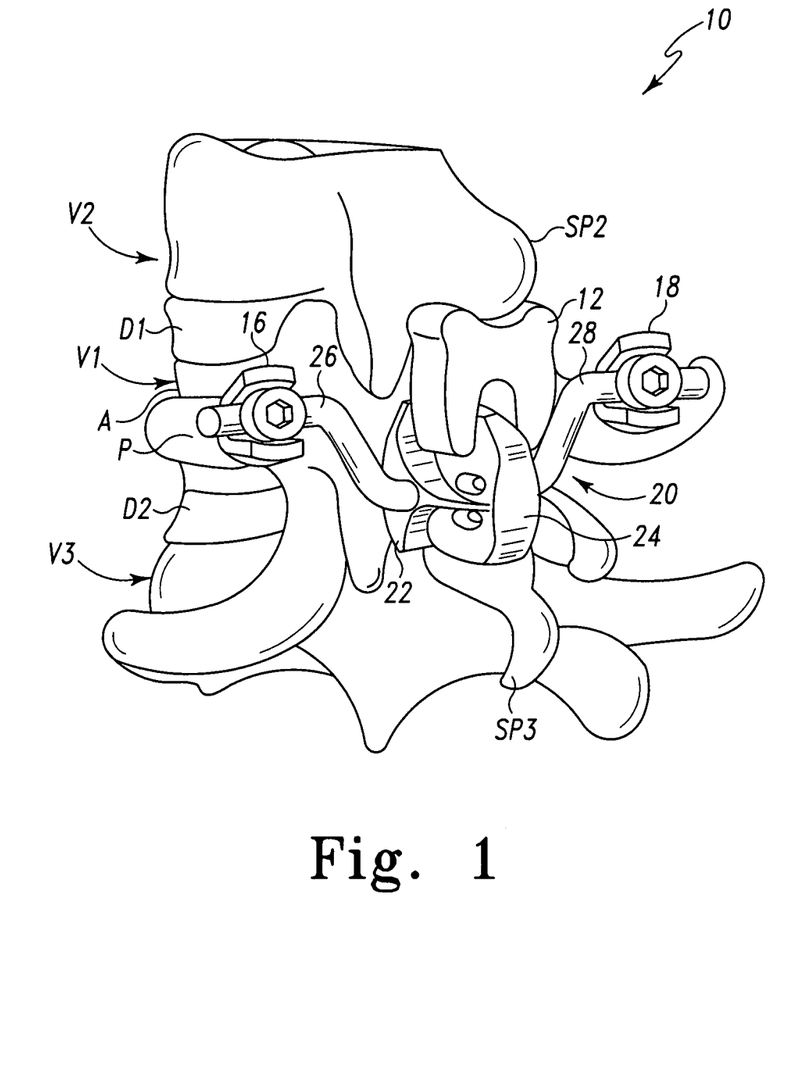
FIG. 1 is a perspective view looking posteriorly at a spinal column segment with a spinous process implant and an interspinous spacer implant engaged thereto.

In FIG. 1 there is shown a spinal column segment 10 with a vertebra V1 having anterior body portion A and posterior elements P. Spinous process implant 20 is engaged to vertebral body V1 along the posterior elements P of vertebra V1. First and second anchors 16, 18 are engaged to the pedicles of vertebra V1 to anchor spinous process implant 20 to vertebra V1. Spinous process implant 20 extends bi-laterally across the sagittal plane of spinal column segment 10 and posteriorly of the spinal canal for connection with anchors 16, 18.

Spinal column segment 10 further includes a superior or cephaladly located vertebra V2 and an inferior or caudally located vertebra V3. Superior disc space D1 is located between vertebrae V1, V2 and inferior disc space D2 is located between vertebrae V1, V3. Superior vertebra V2 includes superior spinous process SP2 and inferior vertebra V3 includes inferior spinous process SP3. Spinous process implant 20 is located between spinous processes SP2, SP3. As further shown in FIGS. 2 and 3, spinous process implant 20 includes a lamina portion 22 adjacent the lamina of vertebra V1 and a spinous process portion 24 extending posteriorly to replace a removed spinous process from vertebra V1. As used herein, anteriorly, posteriorly, superior and inferior are employed to refer to the orientation of spinous process implant 20 when implanted in the patient in the configuration shown in FIG. 1.

An interspinous implant 12 is provided between spinous process SP2 and spinous process implant 20. Interspinous implant 12 is abuttingly engaged with spinous process SP2 and spinous process portion 24 to provide and maintain separation between spinous process SP2 and spinous process portion 24. In one embodiment, interspinous implant 12 is the DIAM™ Spinal Stabilization System of Medtronic, Inc. employed for spinal decompression surgery between spinous processes of the patient to alleviate spinal stenosis. Interspinous implant 12 is placed between the spinous process SP2 and spinous process implant 20 to act as a shock absorber and reduce loads on the surrounding vertebrae and restore the natural function of the joint. The core of interspinous implant 12 can be made of silicone or other compressible, resilient material. The core is surrounded with an outer mesh, and the implant can be tethered to the spinous processes or laminae of the adjacent vertebral bodies. The flexible properties of the interspinous implant 12 may also protect the integrity of the spinous process.

Interspinous implant 12 includes opposite generally U-shaped ends to fit around the respective spinous process and spinous process implant 20. One of the U-shaped ends receives the spinous process SP2 or SP3 therein and the other of the U-shaped ends receives the artificial spinous process implant 20 therein. The U-shaped ends cradle the spinous process implant 20 and spinous process SP2 or SP3 to maintain the interspinous implant 12 in position when positioned therebetween.

Other procedures contemplate that the interspinous implant 12 is made from a rigid or more rigid material such as PEEK, titanium, stainless steel, polymers, metals and metal alloys, or ceramics, or includes any other suitable form for positioning between spinous processes and spinous process implant 20. For example, one form interspinous implant 12 is a plate, clamp or other device that is engaged to spinous process implant 20 and one or more other spinous processes of the patient or other spinous process implants. In yet other embodiments, multi-level stabilization procedures are contemplated by positioning a second interspinous implant 12 between spinous process implant 20 and spinous process SP3. In another embodiment, a single level stabilization procedure is contemplated by positioning a single interspinous implant 12 between spinous process implant 20 and spinous process SP3. In still another procedure, an interspinous implant 12 is positioned between two artificial spinous process implants 20 engaged to respective ones of first and second vertebrae.

Spinous process implant 20 includes replacement body 21 that is formed as a single, integral unit with lamina portion 22 and spinous process portion 24. Other embodiments contemplate that implant 20 includes multiple components assembled or fastened together to form the replacement body. Lamina portion 22 is formed by a plate-like body and includes a flat anterior surface 38 that is oriented toward the spinal canal when implanted and contacts or is positioned adjacent to the lamina of vertebra V1. In other embodiments, lamina portion 22 includes a superior and anteriorly protruding ledge 32 that extends to superior end 50 of replacement body 21, as shown in dashed lines in FIG. 3. Ledge 32 is positionable in contact with or adjacent to any lamina that remains after removal of the spinous process from vertebra V1, and extends superiorly of notch 68 of replacement body 21. As discussed further below, ledge 32 and/or flat anterior surface 38 assists in the formation of a notch in superior end 50 to receive a distraction instrument and prevents the instrument from migrating from the notch into the spinal canal.

Figure 3:
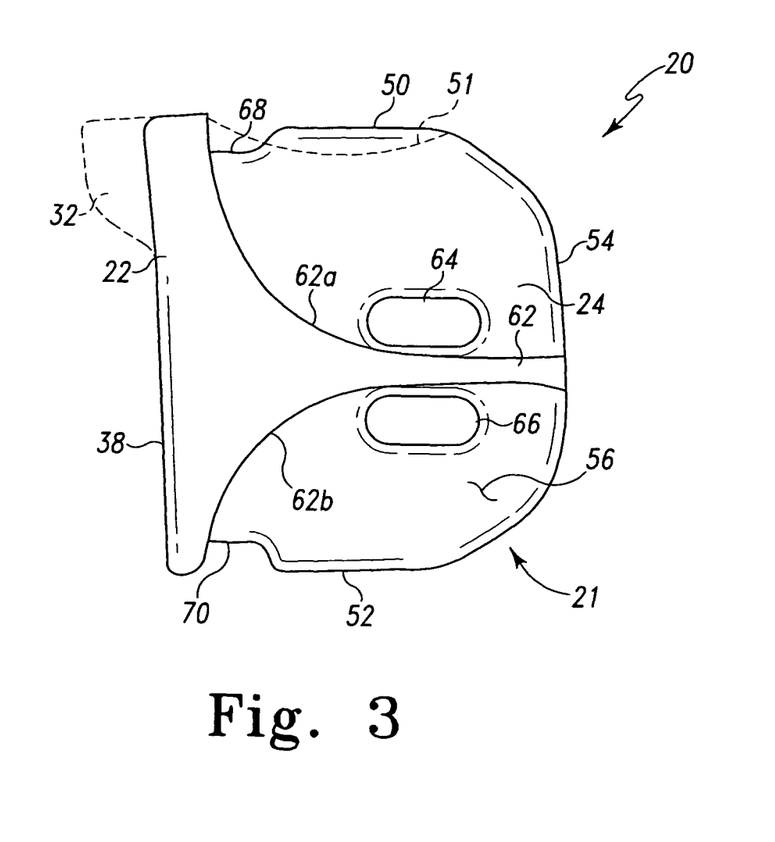
FIG. 3 is a side elevation view of the spinous process implant of FIG. 1 without the connecting elements for clarity in showing the replacement body.

Spinous process portion 24 forms a plate-like posterior extension extending from and transversely oriented to lamina portion 22 to a posterior side 54, and between superior and inferior ends 50, 52. In one form, lamina portion 22 forms a plate-like portion extending orthogonally to the sagittal plane and spinous process portion 24 forms a plate-like portion that lies within or generally parallel to the sagittal plane. Spinous process portion 24 further includes opposite side surfaces 56, 58 extending between lamina portion 22 and posterior side 54, and further extending between superior and inferior ends 50, 52. Opposite side surfaces 56, 58 taper from a maximum thickness adjacent a mid-portion 60 toward the respective ends 50, 52. The tapered side surfaces facilitate engagement with the interspinous implant 12. In other embodiments, non-tapered configurations for opposite side surfaces 56, 58 are contemplated. The transitions between posterior side 54 and superior and inferior ends 50, 52 are beveled as shown in FIG. 3 to eliminate or reduce sharp transitions therebetween and to provide an intimate fit with the interspinous implant.

Spinous process portion 24 also includes a pair of identical opposite support members 62 (only one shown) extending from lamina portion 22 and laterally outwardly from and along side surfaces 56, 58 toward posterior side 54. Support members 62 include a superior support surface 62a and an inferior support surface 62b to provide a location along which the interspinous implant 12 resides against or is positionable into abutting engagement with when engaged to spinous process implant 20. Support surfaces 62a, 62b are concavely curved and form a smooth transition between lamina portion 22 and the portion of support members 60 along spinous process portion 24 to prevent the formation of sharp, abrupt edges and conform to the shape of the interspinous implant to provide a good fit therewith and minimize stress concentrations in the interspinous implant positioned thereagainst. Support members 62 extend along the mid-portion of spinous process portion 24 and divide it into an inferior and superior portion to receive respective adjacent ends of an inferior and superior interspinous implant. In the illustrated embodiment, the height of the superior portion from support members 62 to superior end 50 is slightly greater than the height from support members 62 to inferior end 52 to accommodate the interspinous implants. Other embodiments contemplate other relative heights, including the same heights for the superior and inferior portions.

Spinous process portion 24 also includes a superior through-hole 64 and an inferior through-hole 66 extending between and opening at the respective side surfaces 56, 58. Through-holes 64, 66 provide a location through which tethering elements can be positioned to secure one or two interspinous process spacers to spinous process implant 20. Through-holes 64, 66 are elongated in the anterior-posterior direction when spinous process implant 20 is implanted to provide some adjustability in the tether location therethrough. The elongated through-holes can also accommodate tethers formed as flat, wide bands. Other embodiments contemplate other shapes for through-holes 64, 66, including round through-holes, square or rectangular through-holes, and multiple through-holes in side-by-side relation in the anterior to posterior direction. Still other embodiments contemplate a spinous process implant 20 without through-holes, or an implant 20 with a single through-hole. In still other embodiments, one or both of the through holes includes a side that opens posteriorly in posterior side 54 so that the tether can be side-loaded into the bore.

Spinous process portion 24 also includes a superior notch 68 in superior end 50 and an inferior notch 70 in inferior end 52. Notches 68, 70 provide a secure and reliable location in which a distraction instrument can be received to exert distraction forces between the vertebrae V1 and V2 or the vertebrae V1 and V3 through the artificial spinous process implant 20 and the respect spinous processes SP2, SP3. Notches 68, 70 are formed adjacent the lamina portion 22 so that distraction forces are applied more toward the central axis of the vertebral bodies. Furthermore, lamina portion 22 forms an anterior wall at ledge 32 to prevent the distractor from migrating into the spinal canal during distraction. Notches 68, 70 are U-shaped and are longer in the anterior-posterior direction than their respective depth into spinous process portion 24 to preserve the integrity of spinous process portion 24. Other embodiments contemplate other shapes for notches 68, 70, including V-shapes, semi-circular shapes, and irregular shapes, for example. Still other embodiments contemplate a spinous process implant 20 without notches 68, 70, or an implant 20 with a single notch.

In another embodiment, superior end 50 is formed with a concave, elongated notch 51 extending from lamina portion 22 to or adjacent to posterior side 54, such as shown in dashed lines in FIG. 3. The shallow, elongated notch 51 can accommodate the adjacent end of the interspinous spacer and also accommodate a distractor to facilitate application of distraction forces. Inferior end 52 could also be provided with a concave elongated notch like notch 51.

Figure 2:
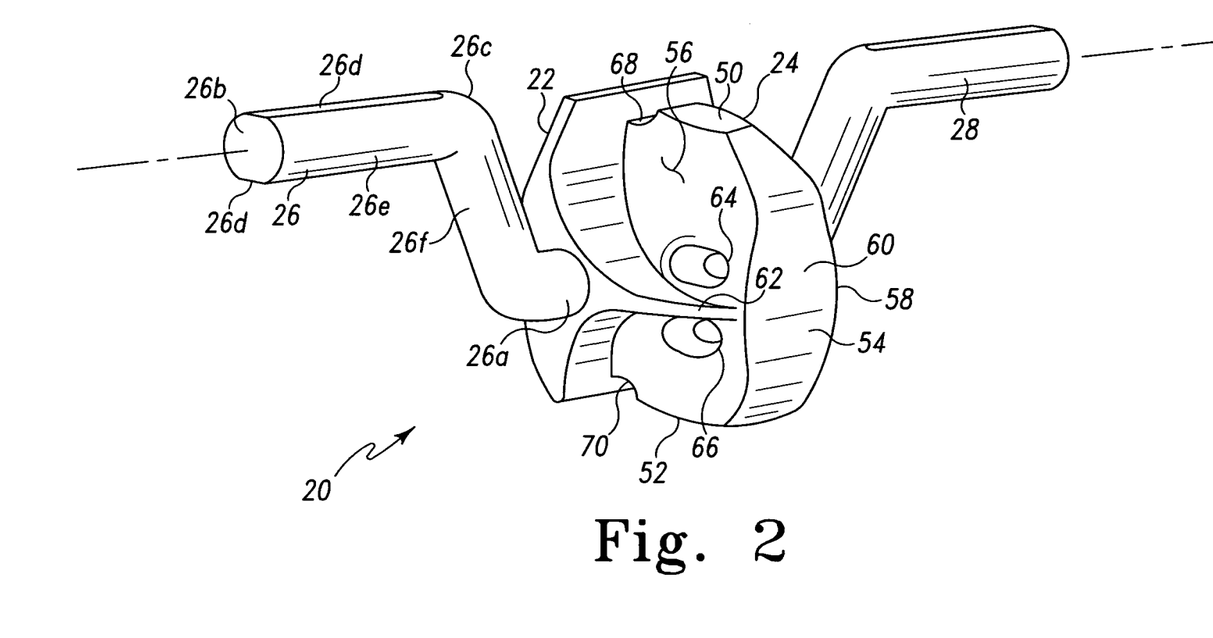
FIG. 2 is a perspective view of the spinous process implant of FIG. 1.

As shown further in FIG. 2, replacement body 21 also includes opposite connecting elements 26, 28 extending from opposite sides thereof in opposite lateral directions when implanted as shown in FIG. 1. Connecting elements 26, 28 are identical to one another, and connecting element 26 will be described with it being understood that connecting element 28 includes the same or similar features. In other embodiments, connecting elements 26, 28 differ from one another. Connecting elements 26, 28 are integrally formed with replacement body 21 in the illustrated embodiment to provide a one-piece implant 20, reducing the handling of multiple components and the associated fiddle factor during surgery. Other embodiments contemplate that one or both of connecting elements 26, 28 are removably attached to replacement body 21 and readily assembled thereto during or prior to implantation.

Connecting element 26 includes an inner end 26a integrally formed with support member 62 where it transitions between lamina portion 22 and spinous process portion 24. Connecting element 26 includes an elongated, rod-like body 26c extending from inner end 26a to an opposite outer end 26b spaced from replacement body 21. Body 26c includes flats 26d along one or more outer surfaces thereof to provide engagement platforms with the respective anchor 16, 18. Flats 26d are arranged to engage the anchor in a keyed arrangement so that rotation of the connecting element 26 in the anchor is prevented by contact of the flats 26d with surfaces in the anchor to prevent rotation of connecting elements 26, 28, and in turn replacement body 21, relative to the respective anchor 16, 18 and vertebra V1. Body 26c includes an outer portion 26e arranged generally orthogonally to the sagittal plane, and an oblique portion 26f extending between outer portion 26e and inner end 26a that is obliquely oriented to outer portion 26e. Oblique portion 26f locates outer portion 26e adjacent to superior end 50 and in a location for engagement with anchors engaged to the pedicle of vertebra V1 when replacement body 21 is located in the desired position.

Outer portions 26e of connecting elements 26, 28 are situated to lie on a common axis L in a linear arrangement. Other embodiments contemplate non-linear profiles for connecting elements 26, 28, as discussed further below with respect to the embodiment of FIG. 4. The outer portions 26e are slidably received in the respective anchor 16, 18 to allow the medial-lateral positioning of replacement body 21 to be adjusted prior to securing the connecting elements 26, 28 in position with respect to the respective anchor 16, 18. Connecting elements 26, 28 can be bent or flexed to contour around the spinal anatomy to facilitate engagement with the respective anchors 16, 18.

Figure 4:
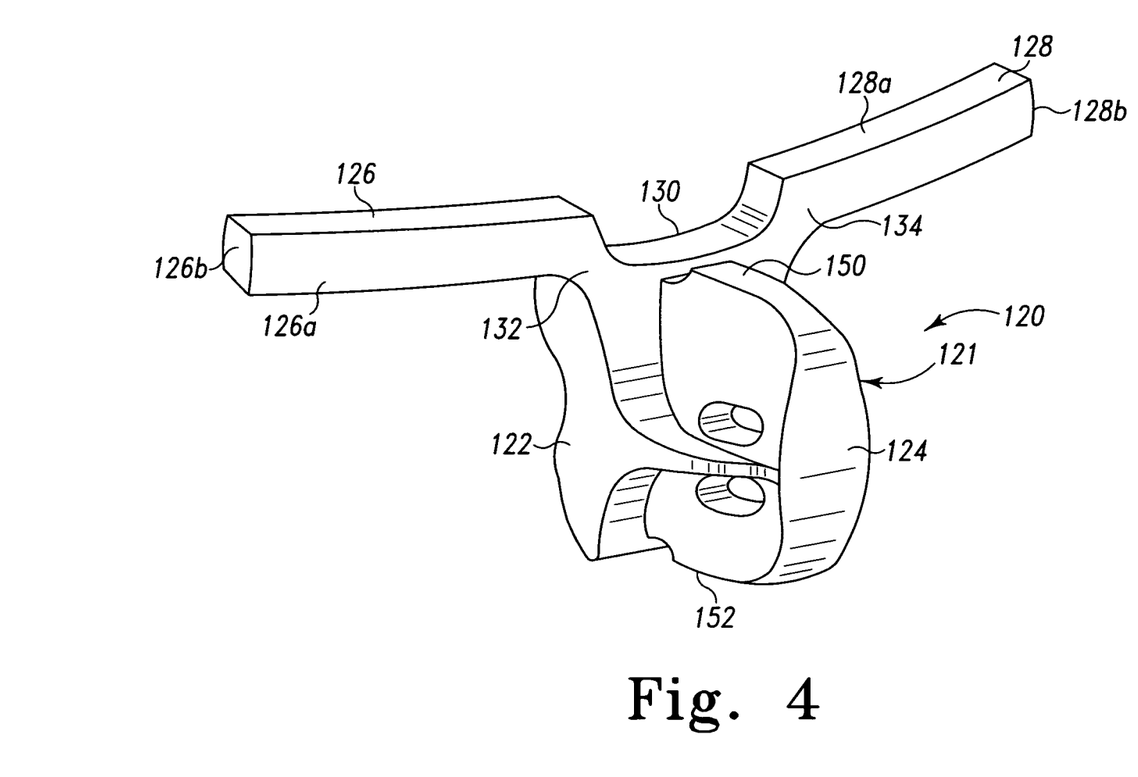
FIG. 4 is a perspective view of another embodiment spinous process implant.

Another embodiment spinous process implant 120 is shown in FIG. 4. Spinous process implant 120 includes a replacement body 121 with a lamina portion 122 and a spinous process portion 124 that are similar to lamina portion 22 and spinous process portion 124 discussed above with respect to spinous process implant 20. However, spinous process implant 120 includes medially-laterally extending connecting elements 126, 128 that are configured differently from connecting elements 26, 28. Specifically, connecting elements 126, 128 each include an ear portion 132, 134, respectively, formed with a corresponding side of lamina portion 122 adjacent to superior end 150. A recess 130 adjacent the superior end 150 of replacement body 121 extends between ear portions 132, 134. Connecting elements 126, 128 also include a body portion 126a, 128a extending from the respective ear portion 132, 134 and away from one another to outer ends 126b, 128b. Connecting elements 126, 128 lie along a curve to extend around the spinal anatomy. The curved profile also allows medial-lateral translation of replacement body 121 while maintaining replacement body 121 in a constant anterior-posterior and cephalad-caudal position with respect to the vertebrae. Outer ends 126b, 128b are located anteriorly of the anterior side of replacement body 121.

Body portions 126a, 128a include an outer surface formed by a series of flat surfaces connected to one another at corners around the respective body portion 126a, 128a to define a non-circular outer surface profile around the respective body portion. The non-circular profile is engaged to the respective anchor 16, 18 in a non-rotating manner so that rotation of replacement body 121 is prevented, maintaining superior and inferior ends 150, 152 in alignment along the vertebra V1.

The replacement bodies and connecting elements of spinous process implants 20, 120 can be made from any suitable biocompatible material. Contemplated materials include metals and metal alloys, polymers, ceramics, elastomers, bone, carbon fiber, and PEEK, for example. The material can be homogenous or composite, and different portions of the implants can be made from different materials to provide desired performance characteristics. The anchors 16, 18 can be any suitable anchor for securing the implant 20, 120 to vertebra V1. In the illustrated embodiment of FIG. 1, anchors 16, 18 are pedicle screws with a distal threaded shaft engaged to the respective pedicle and a proximal receiver connected to the shaft that forms a passage for receiving the respective connecting element therein. An engaging member, such as a set screw, cap, plug, nut, or locking device, is engaged to the receiver to secure the connecting element therein and prevent implant 20, 120 from moving once positioned at the desired location along vertebra V1. Other embodiments contemplate the distal portion of the anchor could be a spinal hook, rod, clamp, staple, post, spinal rod, shaft, interbody implant, or plate, for example. The receiver portion could be a post, clamp, keyway, connector, clamp, or any other suitable device for receiving or engaging the connecting element to the anchor.

In use, spinous process implants 20, 120 are implanted for posterior spinal stabilization with one or more interspinous implants as a stand-alone procedure or in conjunction with other procedures, such as interbody fusion procedures or interbody motion-preserving stabilization procedures. In one procedure, spinous process implants 20, 120 are employed when a spinous process or a lamina of one or more vertebrae is damaged such that it is not capable of supporting an interspinous process implant. Interspinous implant 20, 120 is attached to the damaged vertebrae so that the stabilization procedure with the interspinous spacer can be completed. Interspinous implant 20, 120 allows the surgeon to complete the interspinous stabilization procedure without resorting to an interbody fusion procedure or other suboptimal treatment.

The interbody procedures can be performed in the same or in different vertebral levels than those stabilized with interspinous implant 12 and spinous process implant 20, 120. Implant 20, 120 can be positioned into the patient through a small posterior incision in the patient of sufficient size to admit the implant and instrumentation. Following the incision, muscle and tissue is moved aside if and as needed for removal of one or more compromised spinous processes and placement of the artificial spinous process implant into position along vertebra V1 and into engagement with anchors 16, 18. The connecting elements of implant 20, 120 can be provisionally captured in anchors 16, 18 to allow for slidable medial-lateral adjustment. After the artificial spinous process implant is positioned into the desired location relative to vertebra V1, it is secured in position with anchors 16, 18. Distraction of one or more vertebral levels is then performed as necessary with the artificial spinous process implant 20, 120 and the respective spinous processes SP2, SP3. One or more interspinous implants 12 are then positioned between spinous process implant 20, 120 and the corresponding spinous processes SP2, SP3. Distraction is removed if necessary. One or more tethers are engaged between the interspinous implant 12 and spinous process implant 20, 120 to secure the interspinous implant 12 in position relative to the implant 20, 120 and the supported spinous process SP2, SP3. The interspinous spacer 12 and artificial spinous process implant 20, 120 provide support of the adjacent vertebrae, resisting settling and compression of the space between the vertebrae while allowing at least limited motion of the supported vertebrae.

While the invention has been illustrated and described in detail in the drawings and foregoing description, the same is to be considered as illustrative and not restrictive in character. All changes and modifications that come within the spirit of the invention are desired to be protected.

What is claimed is:

1. An artificial spinous process implant, comprising:
   a lamina portion having a flat anterior surface, the lamina portion defining an anterior side of said implant, said lamina portion extending from a superior end to an inferior end and further including opposite lateral sides extending between said superior end and said inferior end;
   a spinous process portion located between said lateral sides of a posterior face of said lamina portion and extending posteriorly from said lamina portion, said spinous process portion defining a posterior side of the implant and further extending between said superior and inferior ends of said lamina portion and in a transverse orientation to said lamina portion, wherein said spinous process portion includes opposite lateral sides tapering in width from a maximum thickness adjacent to a mid-portion of the spinous process portion toward at least one of said superior and inferior ends of said replacement body;
   a pair of elongated connecting elements extending from said lamina portion in opposite directions from one another, wherein said connecting elements each include an outer end spaced from said lamina portion, said connecting elements extending along a curve so that said outer ends are located anteriorly of said anterior side of said implant, and
   a pair of support members extending from said lateral sides of said lamina portion and along said spinous process portion toward said posterior side of said implant.

2. The implant of claim 1, wherein said support members extend outwardly from respective ones of said opposite lateral sides of said spinous process portion.

3. The implant of claim 1, wherein each of said support members defines a superiorly oriented support surface and an inferiorly oriented support surface that are each concavely curved from said lamina portion along said spinous process portion.

4. The implant of claim 3, wherein said support members are located about mid-height between said superior and inferior ends of said lamina portion.

5. The implant of claim 4, wherein said spinous process portion includes first and second bores extending therethrough in a direction between said opposite lateral sides of said spinous process portion, said first bore being located on a superior side of said support members and said second bore being located on an inferior side of said support members.

6. The implant of claim 5, wherein said first and second bores are elongated in a direction between anterior and posterior sides of said spinous process portion.

7. The implant of claim 1, wherein said spinous process portion includes a bore extending therethrough in a direction between opposite lateral sides of said spinous process portion.

8. The implant of claim 1, wherein said spinous process portion includes a beveled corner extending between a posterior side of said spinous process portion and each of a superior and inferior end of said spinous process portion.

9. The implant of claim 1, further comprising said pair of elongated connecting elements extend from respective ones of said opposite lateral sides of said lamina portion in opposite directions from one another, said connecting elements each being engageable to an anchor engageable to the spinal column of the patient.

10. The implant of claim 9, wherein said connecting elements lie at least in part along a common axis extending between said connecting elements.

11. The implant of claim 10, wherein said connecting elements are linear along said axis.

12. The implant of claim 9, wherein said connecting elements each include an outer portion and an oblique portion obliquely oriented to said respective outer portion and extending between said respective outer portion and an adjacent one of said lateral sides of said lamina portion.

13. The implant of claim 1, wherein said connecting elements each include at least one flat surface extending therealong adjacent an outer end thereof.

14. The implant of claim 13, wherein said connecting elements each include a square cross-section adjacent said outer end thereof.

15. The implant of claim 1, wherein said mid-portion of said spinous process portion is located between superior and inferior ends of said spinous process portion.

16. An artificial spinal process implant, comprising:
a replacement body including a lamina portion having a flat anterior surface, the lamina portion defining an anterior side of said replacement body, said lamina portion extending in a direction from a superior end of said replacement body toward an inferior end of said replacement body, said lamina portion further including opposite lateral sides extending in a direction between said superior end and said inferior end of said replacement body and a spinous process portion having a superior end surface adapted to engage an interspinous process implant and extending transversely to said lamina portion from a posterior face of said lamina portion, said spinous process portion defining a posterior side of said replacement body opposite said anterior side, said spinous process portion further extending in a direction between said superior and inferior ends of said replacement body, wherein said replacement body includes a pair of support members extending from said lateral sides of said lamina portion and along said spinous process portion toward said posterior side of said replacement body, said support members extending outwardly from a respective one of opposite lateral sides of said spinous process portion; and a pair of elongated connecting elements extending in opposite directions from said replacement body and away from said spinous process portion wherein said connecting elements extend along a curve so that outer ends of said connecting elements are located anteriorly of said replacement body.

17. The implant of claim 16, wherein said connecting elements lie along a common axis.

18. The implant of claim 17, wherein said connecting elements are linear along said common axis.

19. The implant of claim 16, wherein said connecting elements each include an outer portion spaced from said replacement body and an oblique portion obliquely oriented to said respective outer portion and extending from said respective outer portion to an inner end integrally fanned with a respective one of said support members.

20. The implant of claim 16, wherein said connecting elements each include an outer portion having at least one flat surface extending therealong.

21. The implant of claim 20, wherein said connecting elements each include a square cross-section along said outer portion.

22. The implant of claim 16, wherein said connecting elements each include an ear portion extending from said lamina portion at said superior end of said replacement body, said connecting elements each further including a body portion extending from said ear portion in opposite directions from one another.

23. The implant of claim 16, wherein said spinous process portion defines at least one notch in at least one of said superior and inferior ends of said replacement body.

24. The implant of claim 23, wherein said at least one notch is located adjacent said lamina portion.

25. The implant of claim 23, wherein said notch forms an elongated, concave recess extending from said lamina portion to said posterior side of said replacement body.

26. The implant of claim 16, wherein said spinous process portion includes at least one through-hole extending between an opening at opposite lateral sides thereof.

27. The implant of claim 16, wherein said support members each define a concavely curved surface extending from said lamina portion and along said respective lateral side of said spinous process portion.

28. The implant of claim 16, wherein said connecting elements and said replacement body are formed as an integral, one-piece unit.

* * * * *